US006524853B1

(12) United States Patent
Kohara et al.

(10) Patent No.: US 6,524,853 B1
(45) Date of Patent: Feb. 25, 2003

(54) VECTOR EXPRESSING THE FULL-LENGTH GENE OF RNA VIRUS AND USE THEREOF

(75) Inventors: Michinori Kohara, Chiba (JP); Kyoko Kohara, Chiba (JP); Kazunari Taira, Ibaraki (JP); Junichi Matsuzaki, Shizuoka (JP); Hiroshi Ohmori, Shizuoka (JP)

(73) Assignee: Chugai Seiyaku Kabushiki Kaisha (JP)

( * ) Notice: Subject to any disclaimer, the term of this patent is extended or adjusted under 35 U.S.C. 154(b) by 0 days.

(21) Appl. No.: 09/720,201

(22) PCT Filed: Jun. 24, 1999

(86) PCT No.: PCT/JP99/03380

§ 371 (c)(1),
(2), (4) Date: Dec. 22, 2000

(87) PCT Pub. No.: WO99/67394

PCT Pub. Date: Dec. 29, 1999

(30) Foreign Application Priority Data

Jun. 24, 1998 (JP) .............................. 10-177820

(51) Int. Cl.⁷ ............................ C12N 5/00; C12Q 1/70; C12Q 1/68; C07H 21/04
(52) U.S. Cl. .............................. 435/325; 435/5; 435/6; 536/23.1; 536/23.72
(58) Field of Search ................ 435/325, 6, 5, 435/69.1; 536/23.1, 23.72

(56) References Cited

FOREIGN PATENT DOCUMENTS

| JP | 6-225770 | 8/1994 |
|----|----------|--------|
| WO | WO 98/21338 | 5/1998 |

OTHER PUBLICATIONS

J.A. Doudna, "Preparation of Homogeneous Ribozyme RNA for Crystallization," *Meth. Mol. Biol.*, 74:365–70 (1997).

J.S. Kieft, et al., "The Hepatitis C Virus Internal Ribosome Entry Site Adopts an Ion–dependent Tertiary Fold," *J. Mol. Biol.*, 292(3):513–529 (Sep. 1999).

J.S. Kieft, et al., "Mechanism of ribosome recruitment by hepatitis C IRES RNA," *RNA*, 7:194–206 (2001).

A.R. Ferré–D'Amaré & J.A. Doudna, "Use of cis–and trans–ribozymes to remove 5' and 3' heterogeneities from milligrams of in vitro transcribed RNA" *Nucleic Acids Res.* 24(5):977–78 (1996).

Been, Michael D. et al., "Self–Cleaving Ribozymes of Hepatitis Delta Virus RNA", Eur J. Biochem 247, pp. 741–753 (1997).

Ball, L. Andrew, "Cellular Expression of a Functional Nodavirus RNA Replicon from Vaccinia Virus Vectors" Journal of Virology, vol. 66, pp. 2335–2345, Apr. (1992).

Grosfeld, Haim et al., "RNA Replication by Respiratory Syncytial Virus (RSV) is Directed by the N, P, and L Proteins; Transcription Also Occurs under These Conditions but Requires RSV Superinfection for Efficient Synthesis of Full–Length mRNA", Journal of Virology, vol. 69, pp. 5677–5686, Sep. (1995).

Ishikawa, Masayuki, et al. "In Vivo DNA Expression of Functional Brome Mosaic Virus RNA Replicons in *Saccharomyces cerevisiae*", Journal of Virology, vol. 71, pp. 7781–7790, Oct. (1997).

*Primary Examiner*—Hankyel T. Park
(74) *Attorney, Agent, or Firm*—Finnegan, Henderson, Farabow, Garrett & Dunner, L.L.P.

(57) ABSTRACT

This invention provides a vector comprising cDNA encoding an RNA viral gene, characterized in that the vector is constructed such that both termini of the RNA viral gene can be transcribed precisely and uniformly. This vector is useful to elucidate the mechanisms of RNA virus replication and of the development of RNA virus infections, and to develop therapeutic agents and means of treatment, and so on.

11 Claims, 7 Drawing Sheets

Expression of the Full Genome HCV-RNA From HCV-Rz

FIG.3
a. RT-PCR
```
5'-GGGCCAGCCC ------------------------------------- 3'
   CCC ---------------------------------------□ A5'-IR
```
Synthesis of cDNA by using Superscript-II
b. Oligo dA tailing with TdT
```
         5'-GGGCCAGCCC ----------------------------- 3'
cDNA --------AAAAACCC-----------------------------□ A5'-IR
```
c. First PCR
```
    CAC-T35
                              A5'-II
CAC -------TTTTTT ◄----------► ■
       -------AAAAAACCC-------------------------□ A5'-IR
```
d. Second PCR
```
    CAC-T35
                              KM2
CAC -------TTTTTT ◄----------► ■
                  1              250bp
```
Cloning and Sequence Expression of HCV-Rz (2-18) in cells

Expression amount of core protein per well

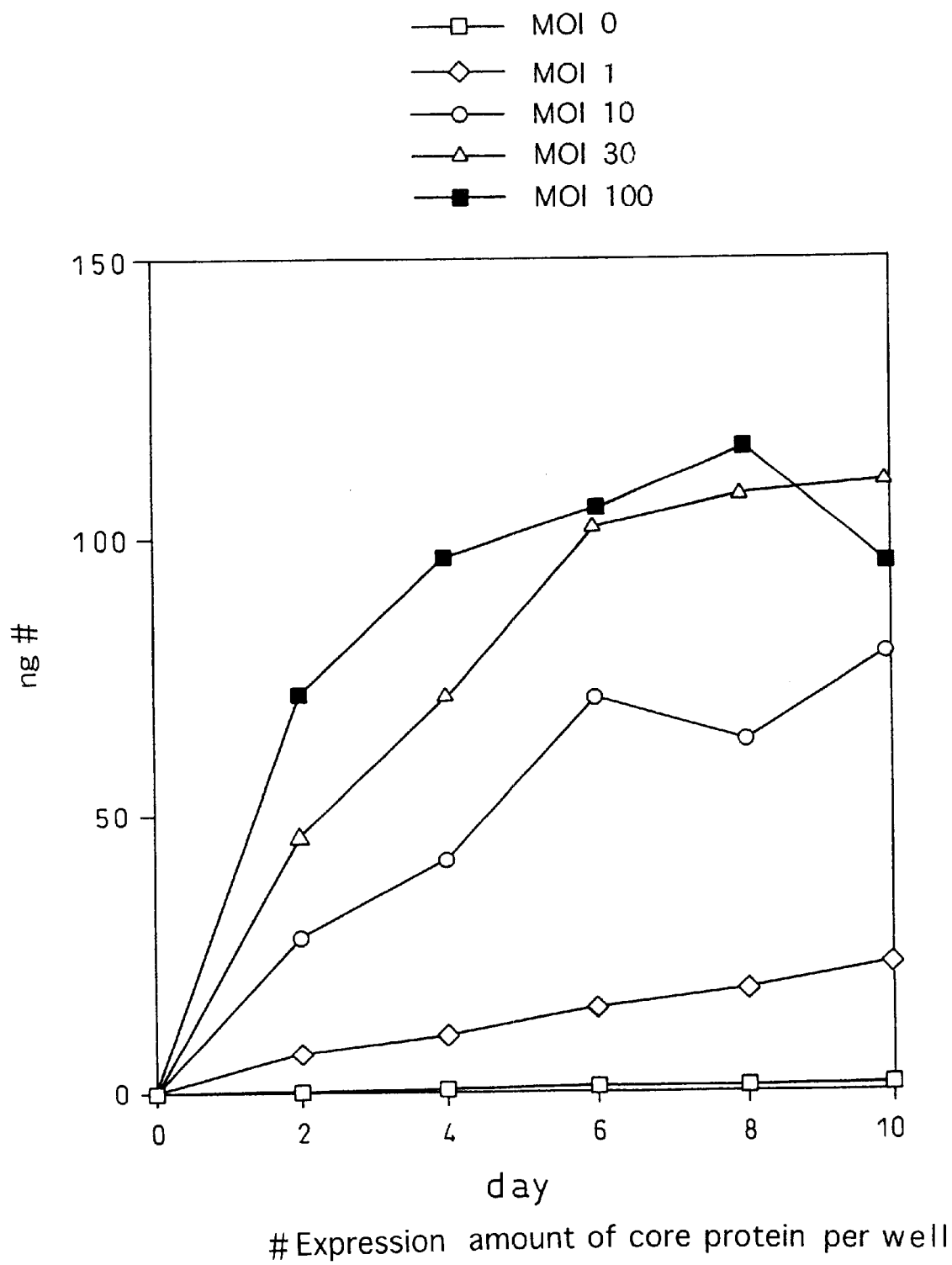

VECTOR EXPRESSING THE FULL-LENGTH GENE OF RNA VIRUS AND USE THEREOF

TECHNICAL FIELD

The present invention relates to a vector which can express the full-length gene of RNA virus, an animal cell and RNA virus infected animal model which comprise the vector, and a method for screening an agent using the cell and the animal model. These are useful to elucidate the mechanisms of RNA virus replication and the development of RNA virus infections, and to develop therapeutic agents and means of treatment, and so on.

PRIOR ART

Hepatitis C virus (hereinafter, HCV) is a principal causative virus in the, development of non-A, non-B post-transfusion hepatitis (Saito, I. et al., *Proc. Natl. Acad. Sci. USA*, 87, 6547–6549 (1990)). Since the hepatitis caused by this virus has high chronicity and may often develop into hepatocirrhosis or hepatoma, this is one of the infections for which the invention of a reliable means of treatment is urgently required. The cDNA of this virus was cloned by Choo et al. in 1989 (Choo, Q. -L., et al., *Science*, 244, 359–362 (1989)), and it is known that the virus is a single-stranded RNA virus belonging to the family Flaviviridae (Kato, N., et al., *Proc. Natl. Acad. Sci., USA*, 87, 9524–9528 (1990)). Several study groups have clarified its total nucleotide sequence and amino acid sequence (Kato, N., et al., *Proc. Natl. Acad. Sci., USA*, 87, 9524–9528 (1990), Proc. Natl. Acad. Sci., USA, 88, 2451–2455 (1991), *J. Virol.*, 65, 1105–1113 (1991), *J. Gen. Virol.*, 72, 2697–2704 (1991), *Virology*, 188, 331–341 (1992)).

Although there are several reports on the establishment of an in vitro infection system of HCV, the real picture is that a stable infection system with repeatability which is practical enough to be utilized for the elucidation of various mechanisms of the virus or the development of means of treatment has not yet established due to problems including low reproduction amounts. (Lanford, R E, et al., *Virology*, 202, 606(1994), Yoo, B J, et al., *J. Virol.*, 69,32(1995), Shimizu, Y K, et al., *Proc. Natl. Acad. Sci. USA*, 89, 5477(1992), Kato, N., et al., *Biochem. Biophys. Res. Comm.*, 206, 863(1995), Batolini, L., et al., *Res. Virol.*, 144,281 (1993)).

On the other hand, there is another method for generating HCV, wherein first an RNA viral genome is generated by transcribing from the corresponding cDNA and then the virus is generated via protein synthesis (Raccaniello, V R, *Science*, 214, 916(1981), *Poliomyelitis* virus). Regarding this method also, several study groups have been working energetically, but there has not been found any practical system, just as in the case of the above-stated infection system (Mizuno, M, et al., *Gastroenterology*, 109, 1933 (1995), Dash, S., et al., *Am. J. Pathol.*, 151,363 (1997)). Furthermore, regarding small animals expressing full-length cDNA such as a transgenic mouse, it has been reported that there is a mouse expressing a part or whole cDNA, but animals which can effectively express all viral proteins are still unknown (Japanese Patent Application Laying-Open (kokai) Nos. 9-9965 and 10-84813).

OBJECTS TO BE ACHIEVED BY THE INVENTION

From the study of the present inventors, the reason why an effective amount of viral particles or viral proteins cannot be generated is considered to be that both termini of the viral genome generated in the process are not transcribed properly so that replicable full-length genes are not generated effectively.

The objects of the present invention are to construct an expression system generating a full-length virus genome, to build up an expression system which resembles more closely the replication of the original virus, and to establish cells or animal models expressing a virus from cDNA using the system.

Means to Achieve the Objects

After thorough study directed to achieve the above objects, the present inventor has succeeded in constructing a vector which can express a full-length RNA viral gene and establishing a cell strain into which the vector is integrated, thereby finally completing the present invention.

That is to say, the first aspect of the present invention relates to a vector which comprises cDNA encoding an RNA viral gene, and the vector is characterized in that it is constructed such that both termini of the RNA viral gene can be transcribed precisely and uniformly.

The second aspect of the present invention relates to an animal cell which is characterized in that it comprises the vector.

The third aspect of the present invention relates to an RNA virus infected animal model which is characterized in that it comprises the vector in a cell thereof.

The forth aspect of the present invention relates to a method for screening an agent inhibiting the replication of an RNA virus wherein the animal cell or the RNA virus infected animal model is used.

This specification includes the contents as disclosed in the specification and/or drawings of Japanese Patent Application No. 10-177820 which are priority documents of the present application.

DISCLOSURE OF THE INVENTION

The details of the present invention are disclosed below.
(1) The First Invention (a Vector)

The vector of the present invention comprises cDNA encoding an RNA viral gene, and is characterized in that it is constructed so that both termini of the RNA viral gene can be transcribed precisely and uniformly. The description "both termini . . . can be transcribed precisely" in this specification means that an RNA produced from cDNA is completely identical to a genomic RNA derived from the virus itself or does not present any differences in nucleotide sequence great enough to influence translation ability. On the other hand, "both termini . . . can be transcribed uniformly" means that the vector can produce with a certain repeatability an RNA having specific nucleotide sequences.

RNA viruses which can be used for the present invention include, but are not limited to, picornavirus such as poliovirus, coxsackievirus and echovirus; reovirus; togavirus including flavivirus such as HCV; orthomyxovirus; paramyxovirus; coronavirus; or plant RNA virus such as tobacco mosaic virus. A preferable RNA virus is HCV.

Methods of transcribing both termini of an RNA viral gene include, but are not limited to, a method wherein DNA encoding a ribozyme which is capable of cleaving the RNA viral gene by self-processing is positioned both upstream of the 5'-terminus and downstream of the 3'-terminus of the cDNA encoding the RNA viral gene.

Ribozymes cleaving an RNA viral gene by self-processing include δ type hepatitis virus (Hepatitis Delta Virus: HDV) ribozyme, hammerhead ribozyme, hairpin ribozyme, artificial ribozyme obtained from in vitro and in vivo selections and the like. Regarding the nucleotide sequence of each of the above ribozymes, there is the description by Eiko Ootsuka et al., *Protein, Nucleic Acid and Enzyme* 40, 1400 (1995). In particular, the nucleotide sequence of HDV ribozyme is disclosed by Suh, Y-A., et al., *Nucleic Acids Research*, 20, 747(1992), and that of hammerhead ribozyme is disclosed by Shimayama, T., et al., *Biochemistry*, 34, 3649(1995). The DNA encoding the ribozyme positioned in a vector can be determined according to the kind and nucleotide sequence of the RNA virus to be used, with reference to the common nucleotide sequences described in these reference documents. Taking HCV as an example, a DNA encoding hammerhead ribozyme at the 5'-terminus side (see sequence X set forth below as an example) and a DNA encoding HDV ribozyme at the 3'-terminus side (see sequence Y set forth below as an example) are considered to be preferable.

SEQ ID NO: X
   CTGATGAGGCCGAAAGGCCGAAACGGCGAA AGCCGTC (SEQ ID NO: 7)

SEQ ID NO: Y
   TGGCCGGCATGGTCCCAGCCTCCTCGCTGGC GCCGGCTGGGCAACATTCCGAOGGGACCGT CCCCTCGGTAATGGCGAATGGGAC (SEQ ID NO: 8)

The vector of the present invention can be produced by, firstly preparing a DNA fragment containing two DNAs encoding the above-described ribozyme and a DNA encoding an RNA virus by PCR or the like, and secondly inserting the DNA fragment into a vector containing a proper promoter and terminator.

The vector of the present invention may express immediately after it was transferred into a host cell, but it is more preferable that the vector initiates expression by a specific treatment. The methods for effecting the initiation of expression by a specific treatment include a method of using a promoter which is not recognized by RNA polymerase of the host cell, a method using Cre/lox expression system (Nat sternberg et al. *J. Molecular Biology* 150. P467–486, Japanese Patent Application Laying-Open (kokai) No. 10-84813) and so on. In the former, the expression of the gene of interest can be initiated by expressing RNA polymerase, which can recognize a promoter in a vector, within the host cell. In the latter method, the expression of the gene of interest can be initiated by expressing Cre enzyme in the host cell.

(2) The Second Invention (an Animal Cell)

The animal cell of the present invention is characterized in that it comprises the vector of the present invention (the first invention).

The animal cell of the present invention can be produced by transferring the vector of the present invention into an animal cell used as a host. Host animal cells include, but are not limited thereto, IMY, HuH-7, HepG2, MOLT-4, MT-2, Daudi, a hepatic primary cell, other hepatocytes, a cell and cell strain derived from hemocyte system cells and the like. The methods for transferring the vector into the host include Lipofection Reagent, but are not limited to this.

(3) The third Invention (an RNA Virus Infected Animal Model)

The RNA virus infected animal model of the present invention is characterized in that it comprises the vector of the present invention in a cell thereof.

The RNA virus infected animal model of the present invention is prepared by a process of transferring the vector of the present invention into zygotes which are then transferred to false parents, obtaining animals derived from the zygotes, and selecting therefrom individuals expressing an RNA virus gene which has integrated.

The introduction into a zygote can be carried out in accordance with standard techniques such as microinjection. The target animals include any of those on which the production technique of the transgenic animal has been established, including mouse, rat, rabbit, pig, cyprinodontidae, zebra fish etc. The individual expressing an RNA virus gene is selected, e.g. by PCR or the like wherein primers prepared on the basis of nucleotide sequences specifically existing in the RNA virus gene are used.

(4) The Forth Invention (a Method for Screening an Agent)

The method for screening an agent inhibiting the replication of an RNA virus of the present invention is characterized in that the animal cell of the present invention (the second invention) or the RNA virus infected animal model of the present invention (the third invention) is used.

When the animal cell is used, the screening can be carried out by adding the target agent to a medium. When the animal model is used, it can be carried out by administering the target agent intravenously or orally.

EXAMPLES

Example 1

Construction of a Vector Expressing Full-length HCV Gene (1) Cloning of HCVcDNA

HCV-RNA was extracted from HCV patient serum R6 (genotype Ib) by AGPC (Chomczynsky, P. et al., Anal. Biochem., 162,156 (1987)), and cDNA was synthesized from the obtained RNA by using SUPERSCRIPT® II kit (Gibco-BRL). The patient serum R6 shows an infectiousness to a chimpanzee (the infectiousness to other experimental animals has not yet been confirmed), and the titer is 10^4.5 CID50 and the PCR value is 10^8.

Among HCV gene sequences (genotype I) reported so far, only the sequences in a highly conserved region were selected, and primers were designed on the basis of them and then were amplified by PCR using Pfu polymerase (Stratagene). Each of these DNA fragments was subcloned into a pBM plasmid according to standard techniques (Maniatis, T., "*Molecular Cloning*, $2^{nd}$ Ed.", CHS Press (1989)) and the nucleotide sequence was determined.

Since HCV easily mutates in the process of cloning, a sequence common to at least 3 clones is considered to be a natural virus sequence, and a full-length clone was constructed by connecting a plurality of such sequences.

The method of constructing the full-length clone is in accordance with the description of Japanese Patent Application Laying-Open (kokai) No. 6-225770.

Preparation of p5'RBZ

First, a DNA comprising EcoRI site, SwaI site, XhoI site, T7 promoter, hammerhead ribozyme and HCV 5'-terminal (1–45 bp) sequence was synthesized by PCR. To enhance the amplification sensitivity and specificity of the DNAs to be detected, Second Step PCR was used. Second Step PCR is a method in which the first cycle is first carried out with 2 types of primers (the first step), then the second cycle is carried out with 2 other types of primers existing inside both termini of the DNA sequence of the first PCR product (the second step). The nucleotide sequence of the PCR primer that was used is shown as follows.

ESXT7RBZ1: 5'-GCC GGA ATT CAT TTA AAT CTC G-3' (SEQ ID NO: 9)

ESXT7RBZ2: 5'-GCC GGA ATT CAT TTA AAT CTC GAG TAA TAC GAC TCA CTA TAG GGC TGG CCC CTG ATG AGG CCG AAA GGC CGA AAC GGC G-3' (SEQ ID NO: 10)

ESXT7RBZ3: 5'-GGG GAG TGA TCT ATG GTG GAG TGT CGC CCC CAA TCG GGG GCT GGC CCG ACG GCT TTC GCC GTT TCG CCC TTT CG-3' (SEQ ID NO: 11)

ESXT7RBZ4: 5'-GGG GAG TGA TCT ATG GTG G-3' (SEQ ID NO: 12)

5 µl of 10×ThermoPol Buffer (10 mM KCl, 20 mM Tris-HCl pH8.8, 10 mM $(NH_4)_2SO_4$, 2 mM $MgSO_4$, 0.1% Triton X-100), 0.5 µl of 20 mM dNTP mixture, 5 µl each of 2 types of primers (ESXT7RBZ2 and ESXT7RBZ3) which were also used as 10 pmol/µl template and 0.5 µl of VENT® DNA polymerase (2 units/µl, New England Biolabs) were added to a 0.5 ml tube, and sterilized water was further added thereto, to prepare 50 µl of the first PCR reaction solution. In this PCR, after the solution was heated at 96° C. for 30 seconds, a cycle of reactions at 96° C. for 30 seconds for denaturation, at 58° C. for 15 seconds for annealing, at 72° C. for 40 seconds for elongation was repeated for 20 cycles. The amplified sequence is shown in SEQ ID NO:1.

Then, 0.5 µl of the first PCR reaction solution, 5 µl of 10×ThermoPol Buffer (10 mM KCl, 20 mM Tris-HCl pH 8.8, 10 mM $(NH_4)_2SO_4$, 2 mM $MgSO_4$, 0.1% Triton X-100), 0.5 µl of 20 mM dNTP mixture, 2 µl each of 2 types of the second step primers (ESXT7RBZ1 and ESXT7RBZ4) and 0.5 µl of VENT® DNA polymerase (2 units/µl, New England Biolabs) were added to a new 0.5 ml tube, and sterilized water was further added thereto, to prepare 50 µl of the second PCR reaction solution. The PCR reaction was carried out under the same conditions as stated above. The obtained PCR reaction solution was subjected to polyacrylamide gel electrophoresis to extract the specifically amplified fragment of interest from the gel. The extraction of the fragment of interest was carried out as follows. First, an ordinary permeable membrane was placed on the gel component side of a chamber, and then a Sartorius permeable membrane was placed on the DNA collecting side thereof. After 2×TBE was put outside the chamber of an electroelution device and 0.1×TBE-0.005% SDS was put inside the same chamber, a cut of gel containing the DNA fragment of interest was placed on the gel component side of the chamber, and several microliters of TE containing Xylene cyanole was added to the DNA collecting component side. Electrophoresis was carried out at 150V for an hour, and then another electrophoresis was carried out again for 45 seconds with a different electrode. The chamber was removed from the electroelution device, and the solution in the chamber was removed until approx. 300 µl of the solution remained in the DNA collecting component side. After collecting 300 µl of the remaining solution, the DNA collecting component was washed with 100 µl and the washing solution was added to the collected solution. The collected solution was extracted with phenol and chloroform, precipitated with ethanol, and dissolved into 10 µl of TE. A portion of the extract was subjected to polyacrylamide gel electrophoresis, and the concentration was estimated to be 20 ng/µl. This PCR product was named ESXT7RBZ PCR product. The amplified sequence is identical to the sequence shown in SEQ ID NO: 1.

Further, DNA positioned from HCV 5'-terminal to a part of the core region (26–613 bp) was synthesized by PCR. The sequences of the PCR primers that were used are as follows.

ESXT7RBZ5: 5'-CCA CCA TAG ATC ACT CCC C-3' (SEQ ID NO: 13)

ESXT7RBZ6: 5'-ATG CCC TCG TTG CCA TAG AG-3' (SEQ ID NO: 14)

10 µl of 10×ThermoPol Buffer (10 mM KCl, 20 mM Tris-HCl pH8.8, 10 mM $(NH_4)_2SO_4$, 2 mM $MgSO_4$, 0.1% Triton X-100), 1 µl of 20 mM dNTP mixture, 4 µl each of 2 types of 10 pmol/µl primers (ESXT7RBZ5 and ESXT7RBZ6), 1 µl of VENT® DNA polymerase (2 units/µl New England Biolabs) and 1 µl of 1 µg/µl template (pT702R6-8) were added to a 0.5 ml tube, and sterilized water was further added thereto, to prepare 100 µl of PCR reaction solution. In this PCR, after the solution was heated at 96° C. for 30 seconds, a cycle of reactions at 96° C. for 30 seconds for denaturation, at 58° C. for 15 seconds for annealing, at 72° C. for 40 seconds for elongation was repeated for 20 cycles. Then, the PCR reaction solution was subjected to agarose gel electrophoresis, and the specifically amplified fragment of interest was extracted from the gel using QIAEX® II Agarose Gel Extraction (QIAGEN). The fragment of interest was extracted as follows. The gel was cut out, 3 times this volume of QX1 buffer was added thereto, then 10 µl of QIAEX® II was added and the solution incubated at 50° C. for 10 minutes. During incubation, shaking was performed every 2 minutes so that QIAEX® II was fully mixed. After the incubation, centrifugation was carried out to remove the surpernatant. Then, the precipitate was washed with PE Buffer twice and air-dried for approx. 15 minutes, 20 µl of sterilized water was added thereto, and the precipitate was suspended again and then incubated at room temperature for 5 minutes. After centrifugation, the supernatant was collected. A portion of the extract was subjected to agarose gel electrophoresis, and the concentration was estimated to be 200 ng/µl. This PCR product was named 5'-HCV PCR product. The amplified sequence is identical to the sequence shown in SEQ ID NO:2.

Using the above-described 2 types of PCR products extracted from the gel (ESXT7RBZ PCR product and 5'-HCV PCR product), the cDNA of interest containing EcoRI site, SwaI site, XhoI site, T7 promoter, hammerhead ribozyme and a sequence positioned from the HCV 5'-terminal to a part of the core region (1–613 bp) was synthesized by PCR. 5 µl of 10×ThermoPol Buffer (10 mM KCl, 20 mM Tris-HCl pH8.8, 10 mM $(NH_4)_2SO_4$, 2 mM $MgSO_4$, 0.1% Triton X- 100), 0.5 µl of 20 mM dNTP mixture, 2 µl each of 2 types of 10 pmol/µl primers (ESXT7RBZ1 and ESXT7RBZ6), 0.5 µl of VENT® DNA polymerase (2 units/µl, New England Biolabs), and as a template 1 µl each of ESXT7RBZ PCR product (4 ng/µl) and 5'-HCV PCR product (4 ng/µl) were added to a 0.5 ml tube, and sterilized water was further added thereto, to prepare 50 µl of PCR reaction solution. In this PCR, after the solution was heated at 96° C. for 30 seconds, a cycle of reactions at 96° C. for 30 seconds for denaturation, at 58° C. for 15 seconds for annealing, at 72° C. for 40 seconds for elongation was repeated for 20 cycles. This PCR product was named 5'-ribozyme PCR product. The amplified sequence is identical to the sequence shown in SEQ ID NO:3

Four volumes of chloroform and three volumes of TE buffer were mixed with 5' ribozyme PCR product followed by centrifugation. The obtained aqueous layer was transferred to a 1.5 ml tube, then 2.35 volumes of 100% ethanol, one quarter volume of 3M sodium acetate, and 1 µl of glycogen (1 µg/µl) were added thereto and precipitated with ethanol (−80° C., 20 minutes). Finally the precipitate was dissolved in 20 µl of sterilized water.

The purified 5' ribozyme PCR product (10 µl) was digested with 1 µl of KpnI in 20 µl of restriction enzyme reaction solution (10 mM Tris-HCl pH7.5, 10 mM $MgCl_2$, 1 mM Dithiothreitol) (37° C., 1.5 hours), 2 µl of 1M sodium chloride was added thereto, and the product was further double-digested with 1 µl of EcoRI (37° C., 2.5 hours).

As a cloning vector, pBM was used. HCV gene may mutate when it replicates, and there is this concern also during cloning. Thus, pBM is a vector constructed to reduce artificial mutations to a minimum which may occur during cloning. A pBM vector was prepared by a process in which a sequence positioned between restriction enzymes EcoRV site and BalI site of pBR322 was deleted with these restriction enzymes, a sequence positioned between EcoRI site and HindIII site of pUC119 multicloning site was integrated into EcoRI/HindIII sites of pBR322, a sequence positioned between VspI site and ScaI site of pBR322 was substituted by a sequence positioned between VspI site and ScaI site of pUC 119, and PstI site existing between these sites was deleted.

After 10 µl of 0.25µg/µl pBM was digested with 1 µl of KpnI at 37° C. for 1.5 hours in 100 µl of restriction enzyme reaction solution (10 mM Tris-HCl pH 7.5, 10 mM MgCl$_2$, 1 mM Dithiothreitol), 10 µl of 1M sodium chloride was added, and the obtained solution was further double-digested with 1 µl of EcoRI at 37° C. for 2 hours. 5 µl of 22 units/µl CIAP (derived from calf small intestine, Takara Shuzo) was added to the enzyme reaction solution and reacted at 37° C. for 30 minutes to remove phosphoric acid from the 5'-terminus.

The 5'-ribozyme PCR product digested with KpnI and EcoRI, and the pBM digested with the same restriction enzymes followed by alkaline phosphatase treating, were subjected to agarose gel electrophoresis to extract the DNA fragment of interest and a cloning vector from the gel QIAEX ® II, and these were dissolved in 20 µl of sterilized water. After a part of these was subjected to agarose gel electrophoresis, the concentration of 5'-ribozyme PCR product (DNA fragment) digested with KpnI and EcoRI was estimated to be 30 ng/µl, and that of pBM (a cloning vector) digested with KpnI and EcoRI followed by alkaline phosphatase treating was estimated to be 20 ng/µl.

1 µl of 5'-ribozyme PCR product (DNA fragment), 1 µl of pBM (a cloning vector), 6 µl of solution I of DNA Ligation Kit Ver.2 (Takara Shuzo) and 4 µl of sterilized water were mixed and a ligation reaction was carried out at 16° C. for 1 hour.

The solution 10 µl obtained by the ligation reaction was added to 100 µl of *Escherichia coli* DH5 α (competent cell), and after it was put on ice for 30 minutes, heat shock was given at 42° C. for 30 seconds. Then, after it was put on ice again for 2 minutes, it was added to 900 µl of SOC medium and incubated at 37° C. for 1 hour. The transformed cells were cultured overnight on a LB-Amp µgate (1% bactotryptone, 0.5% yeast extract, 1% sodium chloride, 1.5% agar, 100 µg/ml ampicillin). Then, each of the colonies that appeared on the plate was cultured at 37° C. for 6 hours in a 13 ml tube containing 4ml of LB-Amp medium (1% bactotryptone, 0.5% yeast extract, 1% sodium chloride, 75 µg/ml ampicillin). Cells were collected by centrifuging the cultured medium, and mini preparation was carried out to obtain DNA plasmids using QIAPREP® Spin Plasmid Kits (QIAGEN) to prepare 20 µl of DNA liquid. The mini preparation was carried out as follows. First, after 250 µl of P1 Buffer was added to a cell pellet, the cell was suspended, then 250 µl of P2 Buffer was further added and mixed, and reacted at room temperature for 5 minutes. Immediately after the reaction, 350 µl of cold N3 Buffer was added thereto, placed on ice for 5 minutes, centrifuged, the supernatant transferred to QIAPREP® Spin column placed in a 2 ml microcentrifuge tube and centrifuged again. The flowthrough fraction was removed, 750 µl of PE Buffer was added to the QIAPREP® Spin column to wash it, followed by centrifugation to remove the flowthrough fraction, and PE Buffer was fully removed by recentrifugation. The QIAPREP® Spin column was transferred to a 1.5 ml tube followed by adding a proper amount of TE, then centrifuged to elute plasmids.

After 16 µl out of the prepared DNA liquid (total amount: 20 µl) was digested with 0.5 µl of KpnI at 37° C. for 40 minutes in 18 µl of restriction enzyme reaction solution (10 mM Tris-HCl pH 7.5, 10 mM MgCl$_2$, 1 mM Dithiothreitol), 2 µl of 1M sodium chloride and 0.5 µl of EcoRI were added and double-digested at 37° C. for 40 minutes. The obtained enzyme reaction solution was subjected to agarose gel electrophoresis to obtain a clone into which the DNA fragment of interest was inserted. This clone was named p5' RBZ.

Preparation of 3' RBZ PCR Product

A DNA containing 3'-terminus of HCV gene (9073–9609 bp), HDV ribozyme, XbaI site, SwaI site and HindIII site was synthesized by PCR. The sequences of the used PCR primers were shown below.

HDRBZ1 5'-TTG GGG TAC CAC CCT TGC G-3'(SEQ ID NO: 15)

HDRBZ2 5'-ACA TGA TCT GCA GAG AGG CC-3' (SEQ ID NO: 16)

HDRBZ3 5'-GGC CTC TCT GCA GAT CAT GTG GCC GGC ATG GTC CCA G-3'(SEQ ID NO: 17)

HDRBZ4 5'-GCC CAA GCT TAT TTA AAT CTA GAG TCC CAT TCG CCA TTA CCG AG-3' (SEQ ID NO: 18)

First, cDNA containing a sequence of 3'-terminus (9073–9609bp) of HCV gene was synthesized by PCR. 5 µl of 10×ThermoPol Buffer (10 mM KCl, 20 mM Tris-HCl pH8.8, 10 mM (NH$_4$)$_2$SO$_4$, 2 mM MgSO$_4$, 0.1% Triton X-100), 0.5 µl of 20 mM dNTP mixture, 0.5 µl of template (N25-3'×+6), 2 µl each of 2 types of 10 pmol/µl primers (HDRBZ1 and HDRBZ2) and 0.51 µl of VENT® DNA polymerase (2 units/µl, New England Biolabs) were added to a 0.5 ml tube, and sterilized water was further added thereto, to prepare 50 µl (×2) of PCR reaction solution. In this PCR, after the solution was heated at 96° C. for 30 seconds, a cycle of reactions at 96° C. for 30 seconds for denaturation, at 58° C. for 15 seconds for annealing, at 72° C. for 40 seconds for elongation was repeated for 20 cycles. This reaction solution was subjected to low-melting agarose gel electrophoresis and a specifically amplified fragment was extracted from the gel using GENE CLEAN® II (Bio 101, La Jolla, Calif.). The extraction with the use of GENE CLEAN® II was carried out as follows. First, a gel containing the DNA fragment of interest was cut out, 3 times the volume of NaI stock solution was added thereto followed by incubation at 50° C. for 10 minutes to melt the gel. Then, 5 µl of GLASSMILK suspension was added, further incubated at 50° C. for 5 minutes, and centrifuged. After the centrifugation, the supernatant was removed, 300 µl of NEW WASH was added to wash the precipitate. After this operation was repeated 3 times, the DNA fragment was eluted by adding 15 µl of sterilized water to the precipitate. A portion of the extracted DNA fragment was subjected to agarose gel electrophoresis, and the concentration was estimated to be 20 ng/µl. This PCR product was named 3' product. The amplified sequence is shown in SEQ ID NO:4.

Next, a cDNA containing 3'-terminus (9590–9609 bp) of HCV gene, HDV ribozyme, XbaI site, SwaI site and HindIII site was synthesized by PCR. 5 µl of 10×ThermoPol Buffer (10 mM KCl, 20 mM Tris-HCl pH8.8, 10 mM $(NH_4)_2SO_4$, 2 mM $MgSO_4$, 0.1% Triton X-100), 0.5 μl of 20 mM dNTP mixture, 0.4 μl of template (Cis-HDV-88), 2 μl each of 2 types of 10 pmol/μl primers (HDRBZ3 and HDRBZ4) and 0.5 μl of VENT® DNA polymerase (2 units/μl New England Biolabs) were added to a 0.5 ml tube, and sterilized water was further added thereto, to prepare 50 μl (×4) of PCR reaction solution. In this PCR, after the solution was heated at 96° C. for 30 seconds, a cycle of reactions at 96° C. for 30 seconds for denaturation, at 58° C. for 15 seconds for annealing, at 72° C. for 40 seconds for elongation was repeated for 20 cycles. This reaction solution was subjected to polyacrylamide gel electrophoresis and the specifically amplified fragment of interest was extracted from the gel. A portion of the extracted fragment was subjected to polyacrylamide gel electrophoresis and the concentration was estimated to be 50ng/μl. This PCR product was named Ribo product. The amplified sequence is shown in SEQ ID NO:5.

Using the above 2 types of extracted PCR products (3' product and Ribo product), the DNA of interest containing 3'-terminus of HCV gene, HDV ribozyme, XbaI site, SwaI site and HindIII site was synthesized by PCR. 5 μl of 10×ThermoPol Buffer (10 mM KCl, 20 mM Tris-HCl pH8.8, 10 mM $(NH_4)_2SO_4$, 2 mM $MgSO_4$, 0.1% Triton X-100), 0.5 μl of 20 mM dNTP mixture, 2 μl each of 2 types of 10 pmol/μl primers (HDRBZ1 and HDRBZ4), 0.5 μl of VENT® DNA polymerase (2 units/μl New England Biolabs), and 2 μl each of 3' product (10 ng/μl) and 5'-Ribo product (5 ng/μl) as a template were added to a 0.5 ml tube, and sterilized water was further added thereto, to prepare 50 μl (×2) of PCR reaction solution. In this PCR, after the solution was heated at 96° C. for 30 seconds, a cycle of reactions at 96° C. for 30 seconds for denaturation, at 58° C. for 15 seconds for annealing, at 72° C. for 40 seconds for elongation was repeated for 20 cycles. Then, 90 μl of PCR product was extracted with phenol and chloroform, precipitated with ethanol and dissolved in 45μl of sterilized water. This PCR product was named 3'-terminal region PCR product. The amplified sequence is shown in SEQ ID NO:6.

After 45 μl out of the total amount of the product was digested with 1.5 μl of KpnI at 37° C. for 45 minutes in 51.5 μl of restriction enzyme reaction solution (10 mM Tris-HCl pH7.5, 10 mM $MgCl_2$, 1 mM Dithiothreitol), 0.5 l of 5M sodium chloride was added thereto, and further double-digested with 1.5 μl of HindIII at 37° C. for 1 hour. After that, the reaction solution was subjected to agarose gel electrophoresis and the specifically amplified fragment of interest was extracted from the gel using QIAEX® II Agarose Gel Extraction (QIAGEN) and was dissolved in 15 μl of sterilized water.

Construction of p5'-3' RBZ

The p5' RBZ was digested with KpnI and HindIII followed by alkaline phosphatase treating and was subjected to agarose gel electrophoresis. The DNA fragment used as a cloning vector was extracted from the gel using QIAEX® II Agarose Gel Extraction (QIAGEN). A portion of the fragment was subjected to agarose gel electrophoresis and the concentration was estimated to be 40ng/μl.

A portion of 3'-terminal region PCR product, which had been digested with KpnI and HindIII and extracted by agarose gel electrophoresis, was subjected to the same electrophoresis again and the concentration was estimated to be 20 ng/μg.

1 μl of 8 ng/μl p5' RBZ (a cloning vector), 1 μl of 20 ng/μl 3'-terminal region PCR product (a DNA fragment), 6 μl of DNA Ligation Kit Ver. 2 (Takara Shuzo) and 4 μl of sterilized water were mixed, and a ligation reaction was carried out at 16° C. overnight. 10 μl of the solution obtained by the ligation reaction was added to 100 μl of *Escherichia coli* DH5 α, and after it was put on ice for 30 minutes, heat shock was given at 42° C. for 30 seconds. Then, it was put on ice again for 2 minutes, added to 900 μl of SOC medium and incubated at 37° C. for 1.5 hours. The transformed cells were cultured overnight on a LB-Amp plate (1% bactotryptone, 0.5% yeast extract, 1% sodium chloride, 1.5% agar, ampicillin(100 μl/ml)). Then, each of the colonies appearing on the plate was cultured at 37° C. overnight in a 13 ml tube containing 4ml of LB-Amp medium (1% bactotryptone, 0.5% yeast extract, 1% sodium chloride, ampicillin(75 μg/ml)). Cells were collected by centrifuging the cultured medium, and mini preparation was carried out to obtain DNA plasmids using QIAPREP® Spin Plasmid Kits (QIAGEN) to prepare 30 μl of DNA liquid. After 20 μl of the DNA liquid was digested with 0.5 μl of HindIII at 37° C. for 40 minutes in 22.8 μl of restriction enzyme reaction solution (10 mM Tris-HCl pH7.5, 10 mM $MgCl_2$, 1 mM Dithiothreitol, 50 mM NaCl), 2.6 μl of 0.5M sodium chloride and 0.5 μl of EcoRI were added, then double-digested at 37° C. for 40 minutes. After the reaction, the solution was subjected to agarose gel electrophoresis and a clone into which the DNA fragment of interest was inserted was obtained.

For the above-stated transforming processes, *Escherichia coli* DH5 α was used in consideration of its simplicity for gene transfer. However, when *Escherichia coli* DH5 α is used as a host cell, there is a possibility that HCV gene mutates when it replicates. Thus, a vector into which the DNA fragment of interest was inserted was transferred to *Escherichia coli* JM109 to obtain a novel transformed cell.

The nucleotide sequence of the DNA fragment inserted into the above obtained clone was analyzed and determined by a DNA sequencing kit Dye Terminator Cycle Sequencing Ready Reaction (PERKIN ELMER). To determine the sequence, first, 8.0 μg of terminator ready reaction mixture, 3 μl of 0.1 μg/μg template DNA and 3.2 μl of 1.0 pmol/μg primer were mixed, and sterilized water was added thereto to prepare 20 μl of sequence reaction solution. In the PCR, after the solution was heated at 96° C. for 5 mitures, a cycle of reactions at 96° C. for 30 seconds for denaturation, at 50° C. for 15 seconds for annealing, at 60° C. for 4 minutes for elongation was repeated for 25 cycles. After the reaction, the solution was purified by CENTRI-SEP COLUMNS (applied Biosystem), then using this as a sample for electrophoresis, sequencing was carried out. A clone having the nucleotide sequence of interest was named p5'-3' RBZ.

Construction of pCALN/5'-3' RBZ

After 24 μg each of p5'-3' RBZ and pCALN/pBR was digested with 41 μl of SwaI (Boehringer Mannheim) individually at 25° C. overnight in 500 μl of enzyme reaction solution, they were treated with TE saturated phenol, phenol/chloroform and chloroform, precipitated with ethanol, and dissolved in 400 μl of TE. The total amount of each solution was subjected to agarose gel electrophoresis, and using QIAEX® II Agarose Gel Extraction (QIAGEN), both approx. 1.3 kbp DNA fragment (p5'-3' RBZ) and approx. 8 kbp DNA fragment used as a cloning vector (pCALN/pBR) were extracted from the gel. Each fragment was dissolved in 96 μl and 222 μl of sterilized water, respectively. A portion of each of these solutions was subjected to agarose gel electrophoresis, and the concentrations of 5'-3' RBZ as a DNA fragment and pCALN/pBR as a cloning vector were estimated to be 70 ng/μl and 35 ng/μl, respectively. To 40 μl of the cloning vector pCALN/pBR, 10 μl of 10×CIAP buffer and 5 μl of 22 units/μl CIAP were added, then sterilized water was further added thereto, to prepare 100 µl of solution. After the solution was reacted with alkaline phosphatase at 37° C. for 30 minutes, it was incubated at 75° C. for 10 minutes to deactivate enzymes. Then, phenol/chloroform treating was carried out 2 times, chloroform treating once, and it was precipitated with ethanol and dissolved in 20 µl of sterilized water. A portion of the solution was subjected to agarose gel electrophoresis and the concentration was estimated to be 25 ng/µl.

2 µl of 70 ng/µl p5'-3' RBZ DNA fragment, 1.5 µl of 25 ng/µl cloning vector pCALN/pBR and 4.5 µl of sterilized water were mixed, incubated at 70° C. for 5 minutes, quenched with ice-cold water immediately followed by adding 2 µl of 5×DNA dilution buffer (Boehringer Mannheim, Rapid DNA Ligation Kit), 10 µl of 2×T4 DNA ligation buffer (Boehringer Mannheim, Rapid DNA Ligation Kit) and 1 µl of 5 units/µl T4 DNA ligase (Boehringer Mannheim, Rapid DNA Ligation Kit), and then a ligation reaction was carried out for 1.5 hours. 2 µl of the solution obtained by the ligation reaction was added to 100 µl of *Escherichia coli* DH5 α, and after it was put on ice for 30 minutes, heat shock was given at 42° C. for 45 seconds. Then, after it was put on ice again for 2 minutes, it was added to 400 µl of SOC medium and incubated at 37° C. for 1 hour. The transformed cells were cultured overnight on a LB-Amp plate (1% bactotryptone, 0.5% yeast extract, 1% sodium chloride, 1.5% agar, 100 µg/ml ampicillin). Then, after each of the colonies that appeared on the plate was cultured a 37° C. for 6.5 hours in a 13 ml tube containing 4 ml of LB-Amp medium (1% bactotryptone, 0.5% yeast extract, 1% sodium chloride, 75 µg/ml ampicillin). Cells were collected by centrifuging the cultured medium, and mini preparation was carried out to obtain DNA plasmids using QIAPREP® Spin Plasmid Kits (QIAGEN), and TE was added thereto, to prepare 50 µl of DNA liquid.

After 15 µl out of the prepared DNA liquid was digested with XbaI at 37° C. for 30 minutes in 20 µl of restriction enzyme reaction solution (10 mM Tris-HCl pH 7.5, 10 mM MgCl$_2$, 1 mM Dithiothreitol, 50 mM NaCl, 0.01% BSA), it was subjected to agarose gel electrophoresis to obtain a clone into which the DNA fragment of interest was inserted. The nucleotide sequence of DNA fragment inserted into the above obtained clone was analyzed and determined by DNA sequencing kit Dye Terminator Cycle Sequencing Ready Reaction (PERKIN ELMER). The clone having the nucleotide sequence of interest was named pCALN/5'-3' RBZ.

Construction of pCALN/HCV RBZ

4 µl of 1 µg/µl pCALN.R6.CR8 was digested with 2 µl of KpnI at 37° C. overnight in 30 µl of restriction enzyme reaction solution (10 mM Tris-HCl pH 7.5, 10 mM MgCl$_2$, 1 mM Dithiothreitol). Then, 4 µl of 0.5M sodium chloride and 2 µl of HindIII were added to 28 µl of the obtained enzyme reaction solution, and sterilized water was further added thereto to prepare 40 µl of solution, and it was digested again at 37° C. for 3.5 hours. After the reaction, the solution was subjected to phenol, phenol/chloroform and chloroform treatings, precipitated with ethanol, and dissolved in 30 µl of TE. A portion of the solution was subjected to agarose gel electrophoresis and approx. 8.5 kbp DNA fragment was extracted from the gel using QIAEX® II Agarose Gel Extraction (QIAGEN) and it was dissolved in 20 µl of sterilized water. Then, the solution was subjected to phenol, phenol/chloroform and chloroform treatings again, precipitated with ethanol, and dissolved in 20 µl of sterilized water.

Similarly, 5 µl of 2 µg/µl pCALN/5'-3'RBZ was digested with 2 µl of KpnI at 37° C. overnight in 30 µl of restriction enzyme reaction solution (10 mM Tris-HCl pH 7.5, 10 mM MgCl$_2$, 1 mM Dithiothreitol). Then, the reaction solution was subjected to phenol, phenol/chloroform and chloroform treatments, precipitated with ethanol, and dissolved in 30 µl of TE. A portion of the solution was subjected to agarose gel electrophoresis and an approx. 9.2 kbp cloning vector was extracted from the gel using QIAEX® II Agarose Gel Extraction (QIAGEN) and it was dissolved in 27 µl of sterilized water. Then, to 27 µl of the subject cloning vector, 5 µl of 10×CIAP buffer and 2 µl of 22 units/µl CIAP were added, then sterilized water was further added thereto, to prepare 50 µl of solution. After the solution was incubated at 50° C. for 30 minutes, it was reacted with alkaline phosphatase. After the reaction, the solution was heated at 75° C. for 10 minutes to deactivate enzymes. Then, phenol/chloroform treatment was carried out twice, chloroform treatment once, and it was precipitated with ethanol and dissolved in 20 µl of sterilized water.

A portion of DNA fragment and cloning vector pCALN/5'-3' RBZ collected from pCALN.R6.CR8 were subjected to agarose gel electrophoresis separately, and the concentration of each solution was estimated to be approx. 20 ng/µg.

4 µl of DNA fragment collected from pCALN.R6.CR8 and 4 µl of cloning vector pCALN/5'-3' RBZ were mixed, and incubated at 80° C. for 3 minutes, quenched with ice-cold water immediately followed by adding 2 µl of 5×DNA dilution buffer, 10 µl of 2×DNA ligation buffer and 1 µl of 5 units/µl T4 DNA ligase, and then a ligation reaction was carried out at room temperature for 1.5 hours. 2 µl of the solution obtained by the ligation reaction was added to 100 µl of *Escherichia coli* DH5 α, and after it was put on ice for 30 minutes, heat shock was given at 42° C. for 45 seconds. Then, after it was put on ice again for 2 minutes, it was added to 400 µl of SOC medium and incubated at 37° C. for 1 hour. The transformed cells were cultured overnight on a LB-Amp plate (1% bactotryptone, 0.5% yeast extract, 1% sodium chloride, 1.5% agar, 100 µl/ml ampicillin). Then, after each of the colonies that appeared on the plate was cultured at 37° C. for 6 hours in a 13 ml tube containing 4 ml of LB-Amp medium (1% bactotryptone, 0.5% yeast extract, 1% sodium chloride, 75 µg/ml ampicillin). Cells were collected by centrifuging the cultured medium, mini preparation was carried out to obtain DNA plasmids using QIAPREP® Spin Plasmid Kits (QIAGEN), and TE was added thereto, to prepare 100 µl of DNA liquid. After 12.5 µl out of the prepared DNA liquid was digested with 1 µl of EcoRI at 37° C. for 30 minutes in 15 µl of restriction enzyme reaction solution (50 mM Tris-HCl pH7.5, 10 mM MgCl$_2$, 1 mM Dithiothreitol, 100 mM NaCl), it was subjected to agarose gel electrophoresis to obtain a clone into which the DNA fragment of interest was inserted.

As a cloned host cell which was constructed to reduce mutations occurring during cloning to a minimum, *Escherichia coli* JM109 was applied instead of *Escherichia coli* DH5 α, thereby a new transformed cell was obtained. Furthermore, taking into consideration the applicability of the vector of the present invention such as transfection to a cell or preparation of tgm, Triton was applied to the following preparation of a plasmid.

First, a large amount of clones was cultured in Super broth (3.3% bactotryptone, 2% yeast extract, 0.75% sodium chloride, 10N sodium hydroxide 1/1000 volumes), and cells were collected by centrifugation at 5,000 rpm for 10 minutes. 1/20 volume of cold TE sucrose (25% sucrose, 50 mM Tris-HCl pH8.0, imM EDTA) was added thereto, followed by transfer to a tube. Then, a series of operations was carried out: 1/100 volumes of 20 mg/ml lysozyme was added on ice and incubated for 5 minutes, 1/50 volume of 0.5M EDTA pH8.0 was added and incubated for 10 minutes incubation, and 2/25 volumes of Triton-lytic mixture (0.1% Triton X-100, 50 mM Tris-HCl pH8.0, 62.5 mM EDTA) was added and incubated for 15 minutes. After these incubations, ultracentrifugation (Beckman roter 45Ti, 30 krpm, 30 minutes, 4° C.) was carried out and the obtained supernatant was transferred to a beaker. Then, to the supernatant, 1/10 volume (w/w) PEG 6000 and 1/10 volume (v/w) of 5M sodium chloride were added and stirred so that they were fully dissolved. After dissolution, it was incubated on ice for 1.5 hours. Then, it was transferred to a centrifugal tube and centrifuged at 8,000 rpm, at 4° C. and for 10 minutes. 3/200 volumes per cultured medium of TE-Sarkosyl(0.4% Sarkosyl, 10 mM Tris-HCl pH7.5, 1 mM EDTA) was added to the obtained precipitate, then 3/200 volumes (w/v) of cesium chloride and 3/8000 volumes of 10 mg/ml of ethylene bromide were further added, and transferred to a centrifugal tube followed by centrifugation at 8,000 rpm, at 15° C. and for 10 minutes. After the centrifugation, a protein membrane formed on the surface of liquid was removed therefrom, a supernatant was transferred to a centrifugal tube, 3/4000 volumes of 10 mg/ml of ethylene bromide was added again. Then, the supernatant was transferred to a ultracentrifugal tube (polyallomer Quick-seal 1×3 ½ in) and ultracentrifuged at 4.8 krpm at 15° C. overnight (Beckman rotor Vti 50). After the ultracentrifugation, plasmids were collected, transferred to a centrifugal tube (polyallomer Quick-seal 1×3 ½ in) again, and ultracentrifuged at 6.5 krpm at 20° C. for 3.5 hours (Beckman rotor Vti80). After the ultracentrifugation, plasmids were collected and extracted with 5M sodium chloride saturated isopropanol 6 times to remove ethylene bromide. After 3 volumes of TE was added to the collected sample, it was precipitated with ethanol and dissolved in a proper amount of TE. The nucleotide sequence of HCV gene inserted into this plasmid was determined by DNA sequencing kit Dye Terminator Cycle Sequencing Ready Reaction (PERKIN ELMER). The plasmid vector having the nucleotide sequence of interest was named pCALN/HCV RBZ (FIG. 1). *Escherichia coli* into which this plasmid was inserted was deposited with the National Institute of Bioscience and Human-Technology, Agency of Industrial Science and Technology (Higashi 1-1-3, Tsukuba-shi, Ibaragi-ken, Japan) under accession No. FERM BP-6763 on Oct. 31, 1997).

Example 2

Confirmation of Expression of a Full-length HCV Gene (1) Confirmation by Northern Blotting pCALN/HCV RBZ was transfected to IMY cell (Itoh, T. et al., submitted) by Lipofection Reagent (GIBCO-BRL) (Felgner, P L, et al., *Proc. Natl. Acad Sci. USA*, 84, 7413 (1987)), was infected with a recombinant vaccinia virus having T7-RNA polymerase (Yasui, K. et al., J. Virol. in press) to express HCV-RNA. Specifically, 18% Lipofection in OPTI-MEM® (Gibco-BRL) was mixed with IMY cell (Rz-DNA 4 mg per 6 cm dish). After it was left at room temperature for 15 minutes, 1.6 ml of OPTI-MEM® was gently added thereto, and seeded on the dish. Then, it was incubated at 37° C. for 5 hours, and a recombinant vaccinia virus with T7 polymerase was adsorbed with MOI=10 for 1 hour. After that, it was cultured at 37° C. for 12 hours to collect infected cells by which the expression of HCV was analyzed. RNA was extracted using Isogen (Nippongene), and 4 μg of the RNA was electrophoresed on formaldehyde gels, transcribed into a nylon membrane (Amersham), and northern blotting was carried out with a solution consisting of 10% dextran sulfate and 1% SDS. 600 bp cDNA corresponding to the region from 5'UTR to the core of HCV gene was labeled with pdCTP to prepare a probe, and an expressed HCV-RNA was detected. Further, as control samples, similar detection was carried out for 2 other cases: where pCALN/HCV RBZ expressed in vitro and also where T702X which does not contain DNA encoding ribozyme expressed. The result is shown in FIG. 2.

When pCALN/HCV RBZ expressed in vitro, HCV-RNA was not trimmed completely and approx. 11 kb RNA was detected. In contrast, when the same vector expressed in a cell, only full length HCV-RNA (9.6 kb) was detected. Further, when T702X was used, full-length HCV-RNA was detected, but the amount was significantly low in comparison with the case where pCALN/HCV RBZ was used.

(2) Confirmation by the use of 5'-Race and 3'-Race

HCV-RNA was extracted from IMY cell into which pCALN/HCV RBZ was transfected and the nucleotide sequences of both termini were examined (FIGS. 1 and 2).

Cloning of 5'-Terminus and its Sequence

To confirm the sequence of the 5'-terminus of the expressed HCV-RNA, the 5' Race method was applied, using 5' Race System (Gibco-BRL). cDNA was synthesized from the extracted HCV-RNA by using A'5-IR primers and SUPERSCRIPT® II kit (Gibco-BRL). The synthesized cDNA was dA-tailed with TdT, and using this as a template, PCR was carried out with CAC-T35 as a sense primer and A5'-II as an antisense primer. Using the obtained amplified product as a template, PCR was carried out again with KM2 as a sense primer and CAC-T35 as an antisense primer. The amplified DNA fragment was cloned into pGEM-T vector (Promega) to determine the nucleotide sequence.

Cloning of 3'-Terminus and its Sequence

After the extracted HCV-RNA was A-tailed with polymerase (Takara), cDNA was synthesized from this HCV-RNA by using CAC-T35 primers and SUPERSCRIPT® II kit. Using the cDNA as a template, the first PCR was carried out with Takara Taq and CAC-T35 primers followed by the second PCR with 3'-X-R6H3 and CAC-T35. The nucleotide sequence of the obtained fragment was determined just as with the 5'-terminus.

The nucleotide sequences of the used primers are as follows.

CAC-T35: CAC(T)$_{35}$ (SEQ ID NO: 19)

KM2: 5'-CTGTACGACACTCATACTAA-3' (SEQ ID NO: 20)

3'-XR6H3: 5'-TTTTTGGTGGCTCCATCTTAGCC-3' (SEQ ID NO: 21)

A5'-IR:5'-GGGTTTGGGATTTGTGCTCATGAT, (SEQ ID NO: 22)

A5'-II:5'-CACTCGCAAGCACCCTATCAGGCAGT, (SEQ ID NO: 23)

Comparing the above sequence result with the nucleotide sequences of both termini of HCV gene, regarding 3'-terminal, a perfect coincidence was observed, but regarding 5'-terminal, the obtained sequence took a form of HCV gene sequence with an additional G. This G is not contained in cDNA inserted into pCALN/HCV RBZ, so it is considered that the G is derived from the cap structure of 5'-terminal of RNA.

(3) Confirmation of the Expression of HCV Protein

Regarding IMY cell to which pCALN/HCV RBZ was transfected, the expression of constitutive proteins was examined by Western blotting (*A New Course of Biochemistry Experiments, Protein I*, Tokyo Kagakudojin (1990)).

IMY cell was solubilized with RIPA buffer (1% SDS, 0.5% NP40, 0.15M NaCl 10 mM Tris-HCl (pH7.4)), was subjected to SDS-PAGE, and transcribed into IMMO-BILON® P (Millipore) with transcription solution (25 mM Tris, 192 mM Glycine, 20% methanol). After that, the membrane was incubated with each of biotinylated monoclonal antibodies (1–2 µl/ml) including anti-core, E1, E2, NS3, NS4A/4B, Ns4B, NS5A and NS5B at 37° C. followed by incubation with avidine-coupled HRPO (Vector stein: 1:1500), and HCV protein was detected with an Amersham membrane ECL®. As a control study, regarding IMY cell to which pCALN/HCV RBZ was not transfected, similarly, the expression of constitutive proteins was examined. The result is shown in FIG. 5 (2–18 in the Figure represents the case where pCALN/HCV RBZ was transfected, and Mock represents the case where pCALN/HCV RBZ was not transfected.)

As the figure shows, specifically conjugating proteins were detected from all the prepared monoclonal antibodies. From this result, it can be said that pCALN/HCV RBZ can express all of HCV proteins.

(3) Example 3

Establishment of HCV Gene Expressed Cell Line

HepG2, IMY cell, and 18% plasmid DNA (4 µl) and Lipofection (GIBCO-BRL) dissolved in OPTI-MEM® (GIBCO-BRL) were mixed, left at room temperature for 15 minutes, 1.6 ml of OPTI-MEM ® was gently added thereto, and seeded on a cell which had been washed with OPTI-MEM ®. After it was left in a $CO_2$ incubator and incubated at 37° C. for 5 hours, the supernatant was substituted by 10% FCS-DMEM (cell cultured liquid). After leaving at 37° C. for 48 hours, the cell was subcultured at a ratio of 1:5, and G418 (800 µg/ml, Bioactive) was added thereto. After approx. 3 weeks, the formed colony was picked up.

Cre-adenovirus was infected to the picked up cell (infective dose: moi=100), and the expression amount of core proteins per well was detected. The result on 3 cell lines of which expression amount were significantly large is shown in FIG. 6.

Subsequently, the infective dose of cre-adenovirus was increased from moi=1 to moi=100, and the expression amount in accordance with the change of infective dose was examined. The result is shown in FIG. 7. As shown in the Figure, the expression amount reached plateau at moi=30. From this result, it is considered that a certain amount of cre enzyme is needed in order that all cells express HCV. Furthermore, in FIG. 7, 2–18 cell lines which expressed HCV the most are shown, but in fact, 2–8 cell lines and 2–22 cell lines also had a similar reactivity.

All publications, patents and patent applications cited herein are incorporated herein by reference in their entirety.

Advantages of the Invention

The present invention provides a vector and the like which can express an RNA viral full-length gene. These are useful to elucidate the mechanisms of RNA virus replication and of the development of RNA virus infections, and to develop therapeutic agents and treating means, and so on.

BRIEF DESCRIPTION OF THE DRAWINGS

FIG. 3 provides a brief description on 5'-Race method.

FIG. 7 shows the relation between the expression amount of Core protein of HCV gene expression cell strain and cre-adenovirus infective dose.

What is claimed is:

1. A vector comprising cDNA encoding an RNA viral gene, wherein said vector is constructed such that both termini of said RNA viral gene can be transcribed precisely and uniformly.

2. The vector of claim 1, wherein DNA encoding a ribozyme which is capable of cleaving the RNA viral gene by self-processing is positioned both upstream of the 5'-terminus and downstream of the 3'-terminus of the cDNA encoding the RNA viral gene.

3. The vector of one of claims 1 and 2, wherein the RNA virus is Hepatitis C virus.

4. An animal cell comprising the vector of one of claims 1 and 2.

5. An animal cell comprising the vector of claim 3.

6. An RNA virus-infected animal model comprising the vector of one of claims 1 and 2 in a cell thereof.

7. The RNA virus-infected animal model of claim 6, wherein the RNA virus is Hepatitis C virus.

8. A method for screening an agent inhibiting the replication of an RNA virus, wherein the animal cell of claim 4 is used therein.

9. A method for screening an agent inhibiting the replication of an RNA virus, wherein the RNA virus-infected animal model of claim 6 is used therein.

10. A method for screening an agent inhibiting the replication of Hepatitis C virus, wherein the animal cell of claim 5 is used therein.

11. A method for screening an agent inhibiting the replication of Hepatitis C virus, wherein the RNA virus-infected animal model of claim 7 is used.

* * * * *

SEQUENCE LISTING

<160> NUMBER OF SEQ ID NOS: 25

Figure 1:
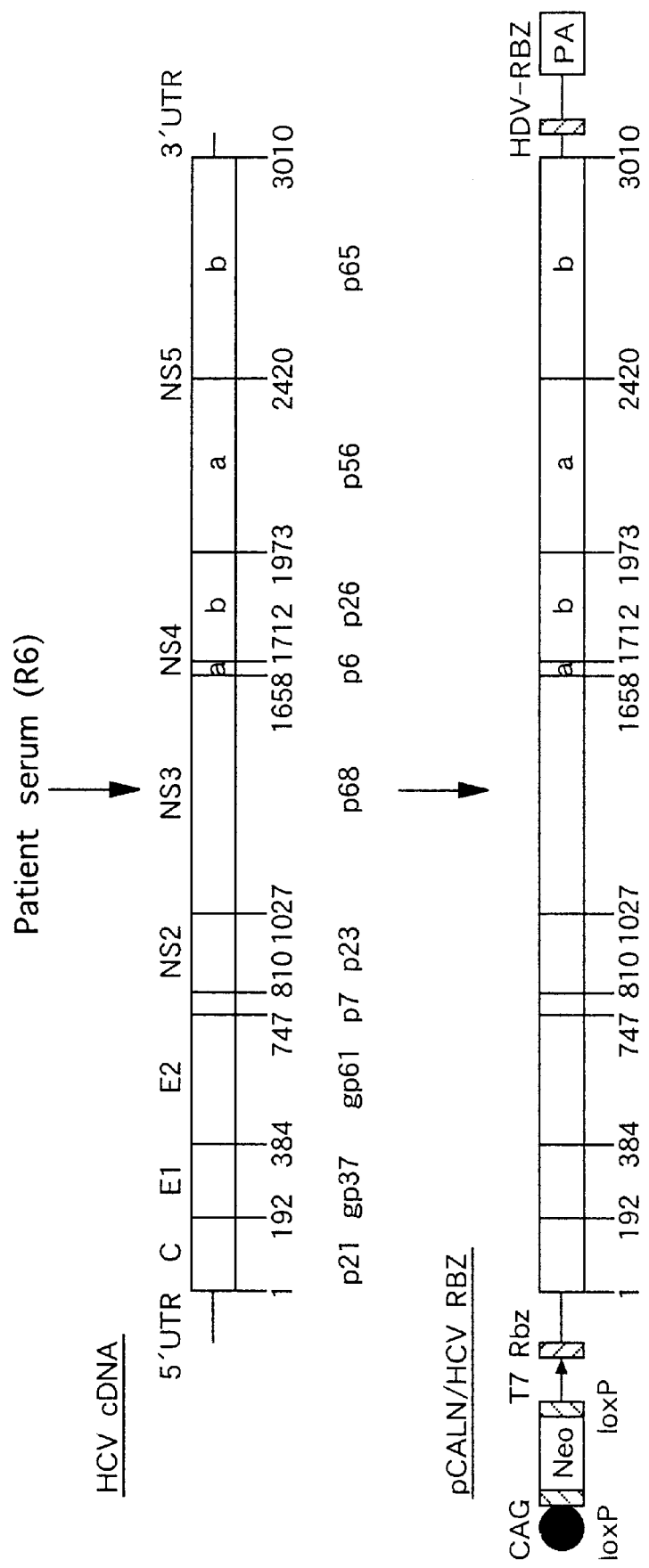
FIG. 1 shows a structure of pCALN/HCV RBZ.
Figure 2:
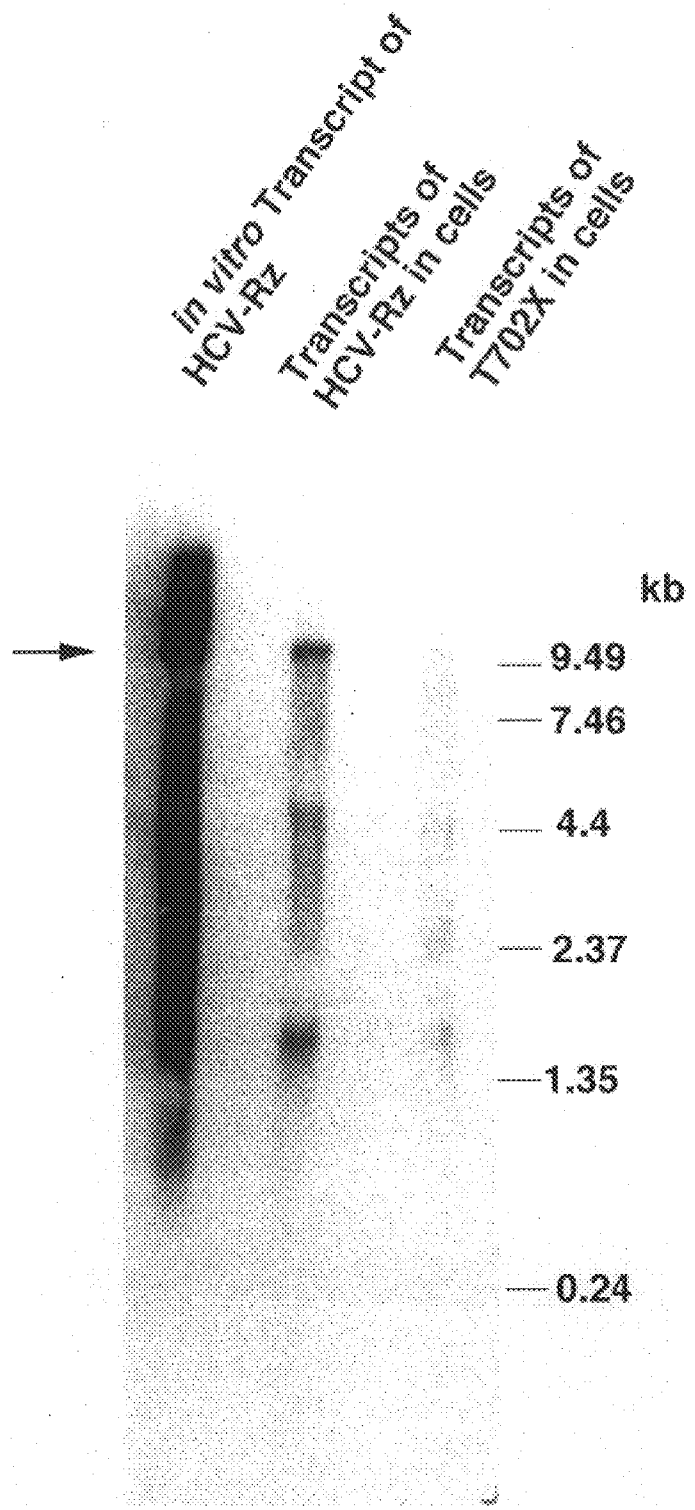
FIG. 2 is a picture which shows a result of Northen blotting carried out for the product transcribed from pCALN/HCV RBZ.
Figure 4:
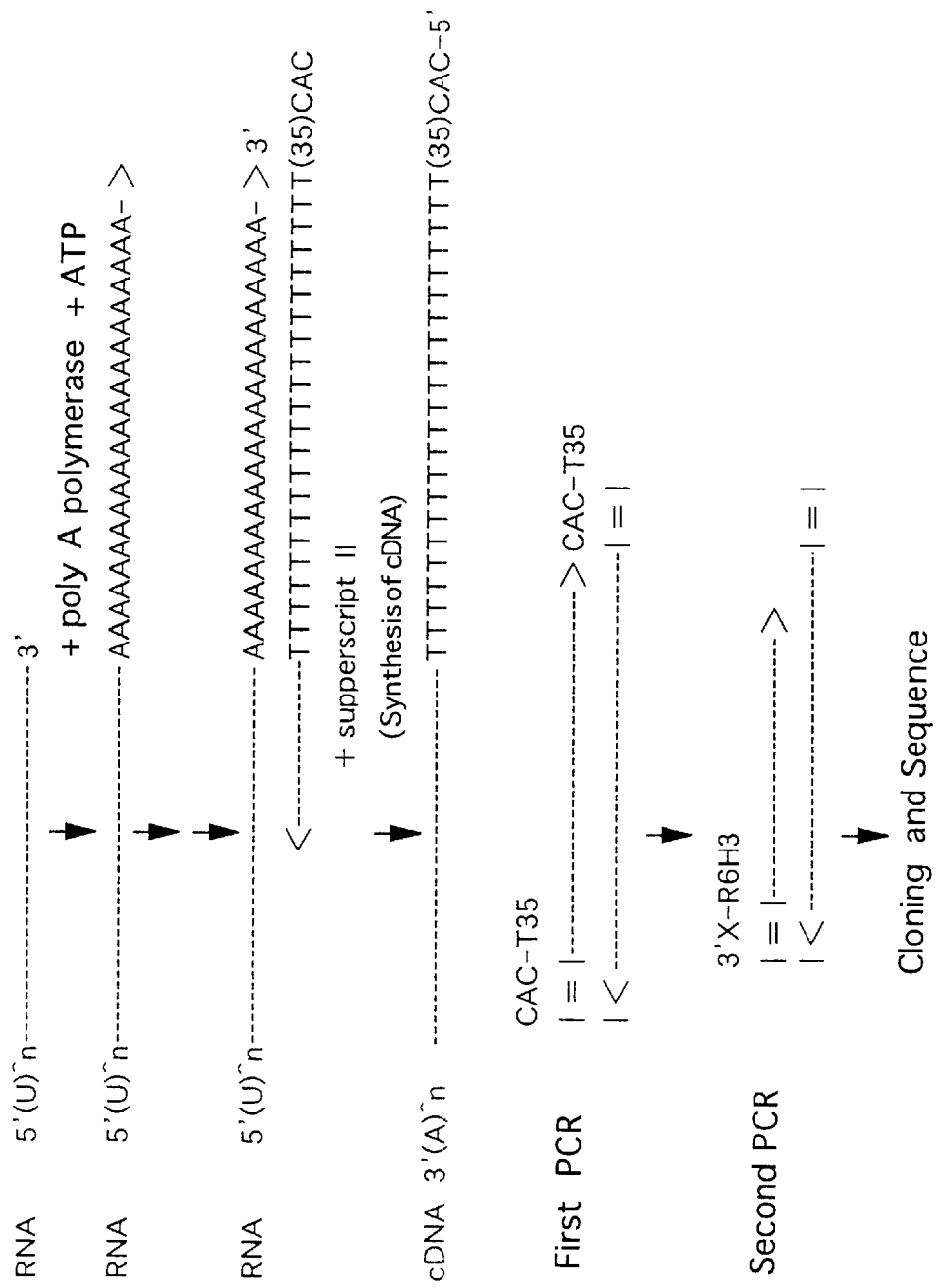
FIG. 4 provides a brief description on 3'-Race method.
Figure 5:
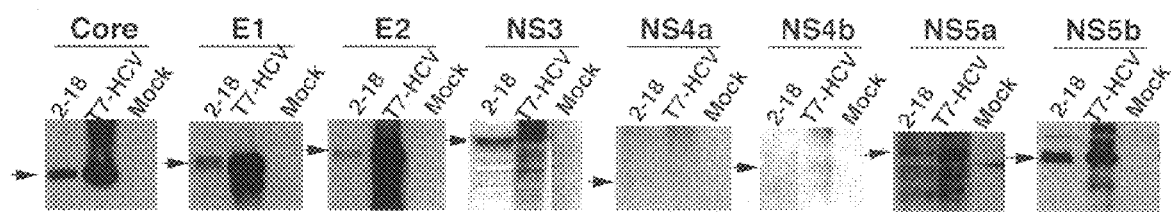
FIG. 5 is a picture which shows a result of Western blotting carried out for the product translated from pCALN/HCV RBZ.
Figure 6:
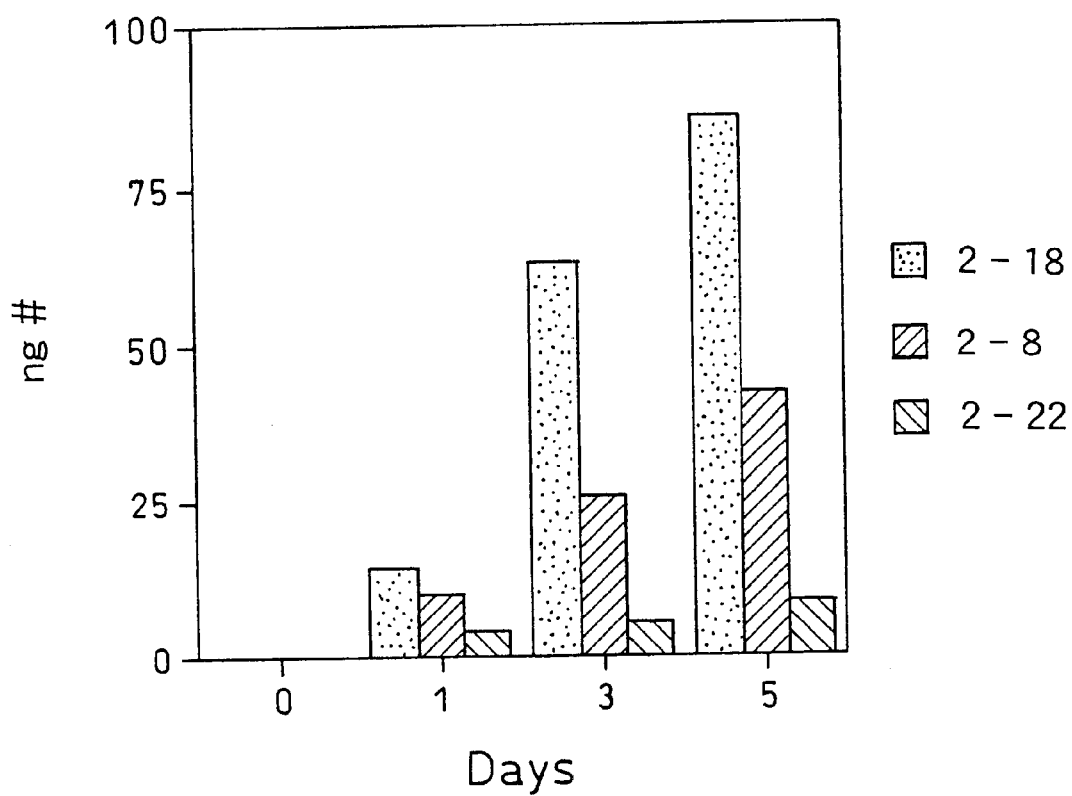
FIG. 6 shows the expression amount of Core protein of HCV gene expression cell strain.

<210> SEQ ID NO 1
<211> LENGTH: 135
<212> TYPE: DNA
<213> ORGANISM: Hepatitus C Virus

<400> SEQUENCE: 1
gccggaattc atttaaatct cgagtaatac gactcactat agggctggcc cctgatgagg     60
ccgaaaggcc gaaacggcga aagccgtcgg gccagccccc gattgggggc gacactccac    120
catagatcac tcccc                                                    135

<210> SEQ ID NO 2
<211> LENGTH: 587
<212> TYPE: DNA
<213> ORGANISM: Hepatitus C Virus

<400> SEQUENCE: 2
ccaccataga tcactcccct gtgaggaact actgtcttca cgcagaaagc gtctagccat     60

-continued

| | |
|---|---|
| ggcgttagta tgagtgtcgt gcagcctcca ggacccccc tcccgggaga gccatagtgg | 120 |
| tctgcggaac cggtgagtac accggaattg ccaggacgac cgggtccttt cttggatcaa | 180 |
| cccgctcaat gcctggagat ttgggcgtgc cccgcgaga ctgctagccg agtagtgttg | 240 |
| ggtcgcgaaa ggccttgtgg tactgcctga tagggtgctt gcgagtgccc cgggaggtct | 300 |
| cgtagaccgt gcatcatgag cacaaatcct aaacccaaa gaaaaaccaa acgtaacacc | 360 |
| aaccgccgcc cacaggacgt caagttcccg gtggtggtc agatcgttgg tggagtttac | 420 |
| ctgttgccgc gcaggggccc caggttgggt gtgcgcgcga ctaggaagac ttccgagcgg | 480 |
| tcacaacctc gtggaaggcg acaacctatc cccaaggctc gccagcccga gggcagggcc | 540 |
| tgggctcagc ccgggtaccc ttggccctc tatggcaacg agggcat | 587 |

<210> SEQ ID NO 3
<211> LENGTH: 702
<212> TYPE: DNA
<213> ORGANISM: Hepatitus C Virus

<400> SEQUENCE: 3

| | |
|---|---|
| gccggaattc atttaaatct cgagtaatac gactcactat agggctggcc cctgatgagg | 60 |
| ccgaaaggcc gaaacggcga aagccgtcgg gccagccccc gattgggggg acactccacc | 120 |
| atagatcact cccctgtgag gaactactgt cttcacgcag aaagcgtcta gccatggcgt | 180 |
| tagtatgagt gtcgtgcagc ctccaggacc cccctcccg ggagagccat agtggtctgc | 240 |
| ggaaccggtg agtacaccgg aattgccagg acgaccgggt cctttcttgg atcaacccgc | 300 |
| tcaatgcctg gagatttggg cgtgcccccg cgagactgct agccgagtag tgttgggtcg | 360 |
| cgaaaggcct tgtggtactg cctgataggg tgcttgcgag tgcccccggga ggtctcgtag | 420 |
| accgtgcatc atgagcacaa atcctaaacc caaagaaaaa ccaaacgta acaccaaccg | 480 |
| ccgcccacag gacgtcaagt tcccgggtgg tggtcagatc gttggtggag tttacctgtt | 540 |
| gccgcgcagg ggccccaggt tgggtgtgcg cgcgactagg aagacttccg agcggtcaca | 600 |
| acctcgtgga aggcgacaac ctatccccaa ggctcgccag cccgagggca gggcctgggc | 660 |
| tcagcccggg tacccttggc ccctctatgg caacgagggc at | 702 |

<210> SEQ ID NO 4
<211> LENGTH: 537
<212> TYPE: DNA
<213> ORGANISM: Hepatitus C Virus

<400> SEQUENCE: 4

| | |
|---|---|
| ttggggtacc acccttgcga gtctggagac atcgggccag aagtgtccgc gctaagctgc | 60 |
| tgtcccaggg ggggagggct gccacttgtg gtaagtacct cttcaactgg gcagtaagga | 120 |
| ccaagctcaa actcactcca atcccggcag cgtcccagtt ggacttgtcc agctggttcg | 180 |
| tggctggtta cagcggggga gacatatatc acagcctgtc tcgtgcccga ccccgctggt | 240 |
| tcatgttgtg cctactccta ctttcagtag gggtaggcat ctacctgctc cccaaccgat | 300 |
| aaacggggag ctaaacactc caggccaata ggccatttct tttttttttt tttttttttt | 360 |
| ttctttttttt tttttttttt tttttttttt tttttttttt tttttctttt cttttgtttt | 420 |
| tttttttttt cttcttttttg gtggctccat cttagcccta gtcacggcta gctgtgaaag | 480 |
| gtccgtgagc cgcatgactg cagagagtgc tgatactggc ctctctgcag atcatgt | 537 |

<210> SEQ ID NO 5
<211> LENGTH: 127

-continued

```
<212> TYPE: DNA
<213> ORGANISM: Hepatitus C Virus

<400> SEQUENCE: 5
ggcctctctg cagatcatgt ggccggcatg gtcccagcct cctcgctggc gccggctggg     60
caacattccg aggggaccgt cccctcggta atggcgaatg ggactctaga tttaaataag    120
cttgggc                                                              127

<210> SEQ ID NO 6
<211> LENGTH: 644
<212> TYPE: DNA
<213> ORGANISM: Hepatitus C Virus

<400> SEQUENCE: 6
ttggggtacc acccttgcga gtctggagac atcgggccag aagtgtccgc gctaagctgc     60
tgtcccaggg ggggagggct gccacttgtg gtaagtacct cttcaactgg gcagtaagga    120
ccaagctcaa actcactcca atcccggcag cgtcccagtt ggacttgtcc agctggttcg    180
tggctggtta cagcggggga gacatatatc acagcctgtc tcgtgcccga ccccgctggt    240
tcatgttgtg cctactccta ctttcagtag gggtaggcat ctacctgctc cccaaccgat    300
aaacggggag ctaaacactc caggccaata ggccatttct tttttttttt tttttttttt    360
ttcttttttt tttttttttt tttttttttt tttttttttt tttttctttt ctttttgtttt   420 tttttttttt cttctttttg gtggctccat cttagcccta gtcacggcta gctgtgaaag    480
gtccgtgagc cgcatgactg cagagagtgc tgatactggc ctctctgcag atcatgtggc    540
cggcatggtc ccagcctcct cgctggcgcc ggctgggcaa cattccgagg ggaccgtccc    600
ctcggtaatg gcgaatggga ctctagattt aaataagctt gggc                    644

<210> SEQ ID NO 7
<211> LENGTH: 37
<212> TYPE: DNA
<213> ORGANISM: Unknown Organism
<220> FEATURE:
<223> OTHER INFORMATION: Description of Unknown Organism: Nucleotide
      sequence encoding hammerhead ribozyme at the
      5'-terminus side

<400> SEQUENCE: 7
ctgatgaggc cgaaaggccg aaacggcgaa agccgtc                              37

<210> SEQ ID NO 8
<211> LENGTH: 85
<212> TYPE: DNA
<213> ORGANISM: Unknown Organism
<220> FEATURE:
<223> OTHER INFORMATION: Description of Unknown Organism: Nucleotide
      sequence encoding HDV ribozyme at the 3'-terminus
      side

<400> SEQUENCE: 8
tggccggcat ggtcccagcc tcctcgctgg cgccggctgg gcaacattcc gagggggaccg    60 tcccctcggt aatggcgaat gggac                                          85

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Primer
```

-continued

<400> SEQUENCE: 9
gccggaattc atttaaatct cg                                                    22

<210> SEQ ID NO 10
<211> LENGTH: 79
<212> TYPE: DNA
<213> ORGANISM: Artificial Sequence
<220> FEATURE:
<223> OTHER INFORMATION: Description of Artificial Sequence: Primer

<400> SEQUENCE: 10
gccggaattc atttaaatct cgagtaatac gactcactat agggctggcc cctgatgagg           60
ccgaaaggcc gaaacggcg                                                        79

<210> SEQ ID NO 11
<211> LENGTH: 74
<212> TYPE: DNA
<213> ORGANISM: Artificial Sequence
<220> FEATURE:
<223> OTHER INFORMATION: Description of Artificial Sequence: Primer

<400> SEQUENCE: 11
ggggagtgat ctatggtgga gtgtcgcccc caatcggggg ctggcccgac ggctttcgcc           60
gtttcggcct ttcg                                                             74

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 12
ggggagtgat ctatggtgg                                                        19

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 13
ccaccataga tcactcccc                                                        19

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 14
atgccctcgt tgccatagag                                                       20

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 15
ttggggtacc acccttgcg                                        19

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 16
acatgatctg cagagaggcc                                       20

<210> SEQ ID NO 17
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 17
ggcctctctg cagatcatgt ggccggcatg gtcccag                    37

<210> SEQ ID NO 18
<211> LENGTH: 44
<212> TYPE: DNA
<213> ORGANISM: Artificial Sequence
<220> FEATURE:
<223> OTHER INFORMATION: Description of Artificial Sequence: Primer

<400> SEQUENCE: 18
gcccaagctt atttaaatct agagtcccat tcgccattac cgag            44

<210> SEQ ID NO 19
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 19 cactttttt tttttttttt tttttttttt tttttttt                   38

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 20
ctgtacgaca ctcatactaa                                       20

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 21
tttttggtgg ctccatctta gcc                                   23

<210> SEQ ID NO 22
<211> LENGTH: 24
<212> TYPE: DNA
<213> ORGANISM: Artificial Sequence

```
<220> FEATURE:
<223> OTHER INFORMATION: Description of Artificial Sequence: Primer

<400> SEQUENCE: 22
gggtttggga tttgtgctca tgat                                          24

<210> SEQ ID NO 23
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 23
cactcgcaag caccctatca ggcagt                                        26

<210> SEQ ID NO 24
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 24
gggccagccc                                                          10

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Poly A
      nucleotide sequence

<400> SEQUENCE: 25
aaaaaaaaaa aaaaaaaaaa aa                                            22
```